(12) United States Patent
Liu et al.

(10) Patent No.: US 8,692,048 B2
(45) Date of Patent: *Apr. 8, 2014

(54) METHOD FOR REVAMPING AN HF OR SULPHURIC ACID ALKYLATION UNIT

(75) Inventors: Zhichang Liu, Changping Beijing (CN); Chunming Xu, Changping Beijing (CN); Rui Zhang, Changping Beijing (CN); Xianghai Meng, Changping Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/388,507

(22) PCT Filed: Aug. 5, 2010

(86) PCT No.: PCT/EP2010/061452
§ 371 (c)(1),
(2), (4) Date: Mar. 13, 2012

(87) PCT Pub. No.: WO2011/015640
PCT Pub. Date: Feb. 10, 2011

(65) Prior Publication Data
US 2012/0165592 A1 Jun. 28, 2012

(30) Foreign Application Priority Data

Aug. 6, 2009 (WO) ................ PCT/CN2009/000889

(51) Int. Cl.
*C07C 7/144* (2006.01)

(52) U.S. Cl.
USPC ............................ 585/899; 585/802; 585/818

(58) Field of Classification Search
None
See application file for complete search history.

(56) References Cited

U.S. PATENT DOCUMENTS

| | | | |
|---|---|---|---|
| 7,285,698 B2 | 10/2007 | Liu et al. | 585/721 |
| 2004/0133056 A1 | 7/2004 | Liu et al. | 585/721 |
| 2005/0119423 A1* | 6/2005 | Bergman et al. | 526/68 |
| 2006/0135839 A1 | 6/2006 | Elomari et al. | 585/721 |
| 2008/0146858 A1 | 6/2008 | Elomari et al. | 585/331 |

FOREIGN PATENT DOCUMENTS

CN 101244972 8/2008

* cited by examiner

*Primary Examiner* — Tam M Nguyen
(74) *Attorney, Agent, or Firm* — Charles W. Stewart

(57) ABSTRACT

The present invention provides a method for revamping an HF or sulphuric acid alkylation unit to an ionic liquid alkylation unit, wherein the HF or sulphuric acid alkylation unit comprise at least: —a reactor unit for contacting catalyst and hydrocarbon reactants; —a separator unit for separating a reactor effluent into a catalyst phase and an alkylate-comprising hydrocarbon phase; —a fractionator unit for fractionating the alkylate-comprising hydrocarbon phase into at least one stream comprising alkylate; and which method includes: —providing a second separator unit suitable for the separation of solids from liquids downstream of the reactor unit suitable to reduce the solids content in at least part of the reactor effluent.

9 Claims, 2 Drawing Sheets

METHOD FOR REVAMPING AN HF OR SULPHURIC ACID ALKYLATION UNIT

PRIORITY CLAIM

The present application claims priority from PCT/EP2010/061452, filed 5 Aug. 2010, which claims priority from PCT/CN2009/000889, filed 6 Aug. 2009.

The present invention provides a method for revamping an HF or sulphuric acid alkylation unit.

There is an increasing demand for alkylate fuel blending feedstock. As a fuel-blending component alkylate combines a low vapour pressure, no olefin or aromatic content with high octane properties.

Almost all alkylate is produced by reacting isobutane with butene in the presence of a suitable acidic catalyst. The most used catalysts are HF (hydrofluoric acid) and sulphuric acid. Although well established, these processes suffer numerous disadvantages. In case of HF, stringent health and safety measures must be applied requiring significant investments. In case of sulphuric acid, the large consumption of catalyst and the need to provide utilities for refrigeration are unfavourable from an economic standpoint.

Recently, the alkylation of isoparaffins with olefins using an ionic liquid catalyst has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor unit and the alkylate is formed by contacting the reactants with a composite ionic liquid under alkylation conditions. The reactor effluent is separated into a hydrocarbon phase and an ionic liquid phase. The ionic liquid phase is recycled to the reactor unit while the hydrocarbon phase is treated to retrieve the alkylate.

Current alkylation units have been specifically designed for either HF or sulphuric acid (also referred to as SA) catalyst and are not optimally suited for use of a different catalyst such as an ionic liquid (also referred to as IL) catalyst. In for instance Liu et al. (Z. Liu, R. Zhang, C. Xu, R. Xia, Ionic liquid alkylation process produces high-quality gasoline, Oil and Gas Journal, vol 104, Issue 40, 2006) it is mentioned that it is possible to retrofit a sulphuric acid alkylation unit for use of an IL catalyst. In Liu et al., it proposed to add a surge tank for IL recycle and to modify the settler internals to enhance separation of the IL. However, it was found by Liu that the performance of the retrofitted alkylation unit was less than optimal.

Therefore, there is a need in the art for an improved method for revamping HF or SA alkylation unit to an IL alkylation unit.

Figure 1:
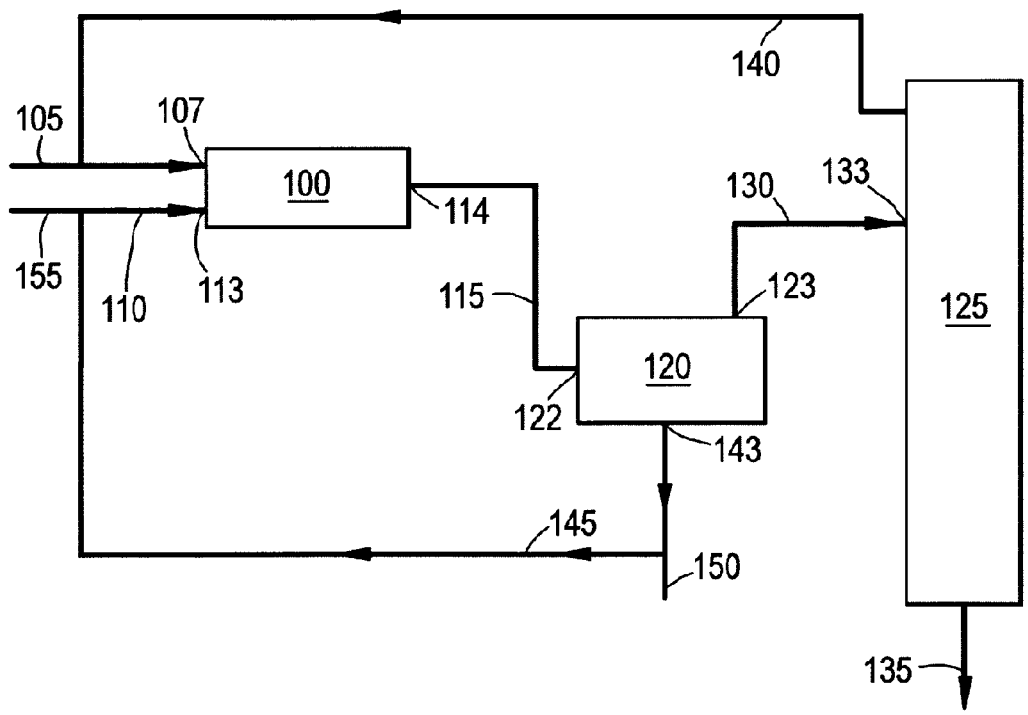
FIG. 1 illustrates a schematic representation of a typical SA alkylation unit.

It has now been found that the less than optimal results reported by Liu et al, are at least in part caused by the formation of solids during the alkylation process. During the operation of an IL alkylation process, solids may be formed. As the reaction progresses, these solids may accumulate in the reaction mixture in the reactor unit.

Therefore the present invention provides a method for revamping an HF or sulphuric acid alkylation unit to an ionic liquid alkylation unit, wherein the HF or sulphuric acid alkylation unit comprise at least:
  a reactor unit for contacting catalyst and hydrocarbon reactants;
  a separator unit for separating a reactor effluent into a catalyst phase and an alkylate-comprising hydrocarbon phase;
  a fractionator unit for fractionating the alkylate-comprising hydrocarbon phase into at least one stream comprising alkylate; and
which method includes:
  providing a second separator unit suitable for the separation of solids from liquids downstream of the reactor unit suitable to reduce the solids content in at least part of the reactor effluent.

The present invention relates to a method for revamping an HF or SA alkylation unit to an IL alkylation unit. Reference herein to revamping is to modifying or adapting an existing unit or process line-up designed for operating a specific process, such that it is suitable for operating another process. The obtained IL alkylation unit is used to produce alkylate by reacting an isoparaffin with an olefin in the presence of an IL catalyst under alkylation conditions. Typical IL alkylation conditions (or process conditions) are known in the art, whereby it will be appreciated that actual operational process conditions are among others dependent of the exact composition of the reactants and catalyst.

The temperature in the reactor unit is preferably in the range of from −20 to 100° C., more preferably in the range of from 0 to 50° C., however the temperature must be high enough to ensure that the ionic liquid is in its liquid form.

To suppress vapour formation in the reactor, the process is performed under pressure, preferably the pressure in the reactor is in the range of from 0.1 to 1.6 MPa.

The alkylation process may be a semi-continues or continuous process. Typically, the isoparaffin is an isobutane or an isopentane and the olefin is an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

In an IL alkylation process, fresh isoparaffins and olefins are supplied to the process in a molar ratio, which is preferably 1 or higher, and typically in the range of from 1:1 to 40:1, more preferably 1:1 to 20:1. In the case of continuous reaction, the excess isoparaffin can be recycled to the reactor unit by recycling one or more isoparaffin-comprising streams.

Reference herein below to downstream is to the direction of the fluid flow path from the reactor unit to the fractionator unit. Reference herein upstream is to the opposite direction, i.e. from the fractionator unit to the reactor unit.

Existing HF and SA alkylation units comprise at least a reactor unit for contacting the reactants with the catalyst. The reactor unit preferably comprises at least one reactant inlet and at least one reactor effluent outlet. Preferably, the reactor unit also comprises at least one catalyst inlet. A typical reactor unit provided in sulphuric alkylation unit is a so-called Stratco contactor. In e.g. a Stratco contactor, the hydrocarbon reactants are introduced into an U-shaped reactor fluid flow path together with the catalyst. For HF alkylation typical reactors include e.g. Stratco contactors, gravity circulation reactors and emulsion reactors.

Generally, cooling tubes are provided in the reactor fluid flow path to remove the heat generated by the exothermic alkylation reaction. Alternatively, cooling is applied to the acid recycle stream. The effluent of the reactor unit is a mixture of catalyst and a hydrocarbon phase, the latter comprising an alkylate and unreacted reactants, predominantly isoparaffin.

The effluent of the reactor unit is normally provided to a separator unit to separate the reactor effluent into a catalyst phase and an alkylate-comprising hydrocarbon phase. Preferably, the separator unit comprises at least one inlet, typically for the reactor effluent or a stream generated there from, and at least one catalyst phase outlet and at least one alkylate-comprising hydrocarbon phase outlet.

The separator unit serves to separate the effluent of the reactor unit into an alkylate-comprising hydrocarbon phase and a catalyst phase. Preferably, the separator unit used in the HF and SA alkylation units to be revamped is a settler unit. Due to the low affinity of the HF and SA catalyst for hydrocarbons, the two phases separate readily under the influence of gravity. Reference herein to a settler unit is to any separator unit that separates two liquid phases under the influence of gravity. Actually, HF, SA and IL catalysts all have a density, which is higher than that of the hydrocarbon phase, therefore the reactor effluent is typically separated in the settler in an upper hydrocarbon phase and a lower catalyst phase.

In case of SA alkylation, catalyst phase recycle means are provided to recycle SA catalyst from the settler unit to the reactor unit. Typically, to maintain catalyst activity, part of the SA catalyst is removed from the process as spent catalyst and fresh SA catalyst is added to keep catalyst levels and activity intact.

In case of HF alkylation, the HF catalyst is regenerated and recycled to the process for reuse. For this reason, an HF alkylation unit comprises catalyst phase recycle means to recycle the HF catalyst, combined a separate regeneration.

In both SA as HF alkylation, the alkylate-comprising hydrocarbon phase, which was obtained in the settler is, at least in part, provided to a fractionator unit to obtain the retrieve the alkylate. The fractionator unit preferably comprises at least one alkylate-comprising hydrocarbon phase inlet. The fractionator unit, typically, comprises one or more distillation sub-units, including for instance a main fractionator (also referred to in the art as iso-stripper), an acid stripper and/or a depropaniser.

Following the fractionation, the obtained alkylate may be used to prepare avgas or as a blending component for gasoline. The hydrocarbon phase may also comprise significant amounts of unreacted isoparaffin. Preferably, such isoparaffin is at least partly recycled back to the reactor unit, via a provided means for recycling isoparaffin from the fractionator unit to the reactor. Other hydrocarbon streams may also be obtained by fractionation of the hydrocarbon phase, such a n-paraffin-comprising stream.

In existing HF or SA alkylation units means are provided to allow the reactants and catalyst to enter the reactor and to provide the reactor effluent to the separator unit and subsequently the alkylate-comprising hydrocarbon phase to the fractionator unit. It is not necessary to pass the reactor effluent directly from the reactor unit to the separator unit. The reactor effluent may undergo intermediate treatment such as cooling or heating in a heat exchanger. The same applies for the alkylate-comprising hydrocarbon phase being provided to the fractionator unit. Typically, a fluid flow path for the reactants, products and catalyst is created by providing means to introduce reactants and catalyst to the reactor unit. In addition, means are provided to provide reactor effluent from the reactor effluent outlet of the reactor unit to the reactor effluent inlet of a separator unit located downstream from the reactor unit in the fluid flow path. Also, means are provided to provide an alkylate-comprising hydrocarbon phase from the alkylate-comprising hydrocarbon phase outlet of the separator unit to the alkylate-comprising hydrocarbon phase inlet of a fractionator unit located downstream from the separator unit in the fluid flow path and catalyst phase recycle means are provided to recycle catalyst from the settler unit to the reactor unit.

Ionic liquids are known in the art for their ability to catalyse alkylation reactions. The catalyst used in the present invention is a composite ionic liquid comprising cations derived from a hydrohalide of an alkyl-containing amine, imidazolium or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium ($NEt_3H^+$) and methyl-diethyl-ammonium cations ($MeNEt_2H^+$) or

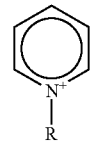

The anions of the composite ionic liquid are preferably aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples or suitable metals include copper, iron, zinc, nickel, cobalt, molybdenum, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

In the method according to the present invention solids, formed during the alkylation process are removed. By removing at least part of the solids formed during the alkylation reaction, the accumulation of solids in the reaction mixture may be prevented.

Reference, herein to solids is to non-dissolved solid particles. In HF or SA alkylation processes, no significant amounts, if any, of solids are produced. Therefore, no means are provided to remove these solids.

The solids predominantly consist out of metals, metal compounds and/or metal salts, which were originally comprised in the acidic liquid catalyst. Additionally, the solids may comprise compounds, which were formed by a chemical reaction including any of the above-mentioned compounds. Typically, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise components, which were introduced into the reaction mixture as contaminants in the hydrocarbon mixture or the acidic ionic liquid.

The solids may have any size, however it was found that the solids typically have an average size of in the range of from 0.1 to 10 µm. In particular, at least 50% of the solids have a particle size below 5 µm, more particular 80% of the solids have a particle size below 5 µm based on the total number of solid particles.

Although, during the alkylation reaction in the reactor unit, the solids may be dispersed, upon separation of the reactor effluent in the settler unit it has been found that the solids, i.e. to a large extent, accumulate in the IL catalyst. This is due to the high density of the solids. The IL catalyst is subsequently recycled to the reactor unit together with the solids. As a result, the solids accumulate in the reactor unit, resulting in undesirable solids content in the reactor unit, but also in the reactor effluent. A high solids content in the reaction mixture may for instance result in blockage of pathways or valves in the reactor unit and pipes to and from the separator unit, due to precipitation of solids. In addition, at high solids content the solids may agglomerate to from large aggregates, resulting in increased blockage risk.

In the method according to the present invention a second separator unit, suitable for the separation of solids from liquids is provided. Such a second separator unit may be any separator unit suitable for the separation of a solid from a liquid, including but not limited to filtration, precipitation and centrifugation units. Such processes are well known in the art. The second separator unit, comprises an inlet for a solids comprising stream, an outlet for a solids depleted stream and an outlet for a solids comprising stream. It will be appreciated that the second separator unit may be comprised of two or more similar or different separation sub-units suitable for the separation of a solid from a liquid. Preferably, the second separator unit comprises one or more centrifugal separator units.

Due to the specific nature of the IL catalyst it is preferred that the removal of the solids is performed at such a temperature that the IL catalyst is liquid. Preferably, the second separator unit can be operated at a temperature in the range of from 5 to 80° C., more preferably of from 20 to 60° C. By removing the solids at elevated temperatures, the viscosity of the IL is lower while the density of the IL is reduced, which may be beneficial in view of the decreased time and power input required to obtained separation of the solids from the liquid.

The second separator unit may be provided at any suitable place in the HF or SA alkylation unit, which is revamped. The second separator unit may be integrated with the reactor unit to remove the solids directly from the reaction mixture inside the reactor. However, preferably, the second separator unit is provided downstream of the reactor unit. For instance, upstream of the first separator unit, i.e. the settler unit for separation the hydrocarbon phase from the catalyst. In this way at least part of the reactor effluent may be treated to remove the solids. However, as mentioned herein above, the solids accumulate in the catalyst phase in the settler unit. Therefore, it is more preferred to remove the solids from the catalyst prior to reintroducing the catalyst into the reactor unit, i.e. downstream from the settler unit in the catalyst phase recycle means. In case of a revamp of an HF or SA alkylation unit this can be done by adapting the catalyst phase recycle means by providing a second separator unit suitable for separating solids from a liquid.

It is not required to remove all solids. Preferably, solids are removed to an extent that the reactor unit comprises at most 5 wt %, preferably in the range of from 0.05 to 5 wt %, more preferably of from 0.1 to 2 wt % of solids based on the total weight of the ionic liquid catalyst in the reactor unit.

Although, it is believed that part of the catalyst is lost when forming the solids, the catalyst alkylation performance is not significantly affected. Loss of the catalyst due to solids formation merely means that a small fraction of the total catalyst inventory is inactivated, while the remainder of the catalyst remains unaffected.

The solids may be removed from the process in any form, typically the solids will be removed in the form of a slurry of solids. Such a slurry may comprise next to the solids for instance some residual acidic ionic liquid. Preferably, means are provided to further treat the slurry by extracting the residual acidic ionic liquid. This is preferably done using a liquid-liquid extraction process with a suitable solvent. Due to the virtual absence of an ionic liquid vapour pressure, the solvent can be easily recovered by for instance evaporation and subsequent condensation. The recovered solvent can be reused.

The solids, which are removed from the process may be discarded, however it is preferred to reuse the components in the solids, for example in the preparation of fresh IL catalyst.

In FIG. 1 a schematic representation is given of a typical SA alkylation unit not according to the invention.

In FIG. 1, a hydrocarbon mixture, comprising olefin and isoparaffin is provided to reactor unit 100, e.g. a Stratco contactor, via conduit (e.g. a pipe) 105, through reactant inlet 107. Catalyst, SA or IL, is also provided to reactor unit 100 through conduit 110 and catalyst inlet 113. In reactor unit 100, the hydrocarbon mixture and catalyst are contacted under alkylation conditions. Through reactor effluent outlet 114, a reactor effluent comprising catalyst and hydrocarbons is withdrawn from reactor unit 100 and supplied via conduit 115 to settler unit 120 through reactor effluent inlet 122. In settler unit 120, an alkylate-comprising hydrocarbon phase and a catalyst phase separate under influence of gravity. The hydrocarbon phase is withdrawn from separator unit 120 via alkylate-comprising hydrocarbon phase outlet 123 and provided to fractionator unit 125 through conduit 130 and alkylate-comprising hydrocarbon phase inlet 133. From the bottom of fractionator unit 125, an alkylate-comprising product is retrieved through conduit 135. The alkylate product can for instance be used for fuel blending purposes. Additionally, an isoparaffin product is retrieved from fractionator unit 125, which is recycled via conduit 140 to become part of the hydrocarbon mixture in conduit 105. Other hydrocarbon-comprising streams (not shown) may also be retrieved from fractionator 125.

The catalyst phase is withdrawn from separator unit 120 through catalyst phase outlet 143 and can be recycled via catalyst phase recycle conduit 145 to reactor unit 100. A spent catalyst fraction may be withdrawn from the process via conduit 150. Additional fresh catalyst can be provided to reactor unit 100 via conduit 155

Figure 2A:
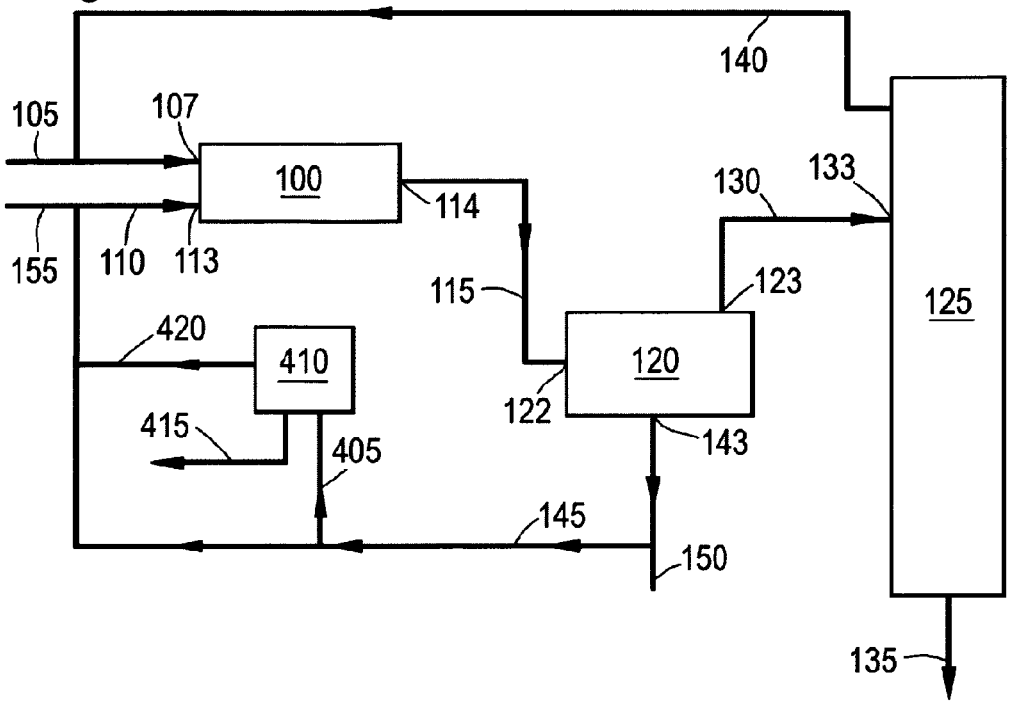
FIG. 2A illustrates a schematic representation of an SA alkylation unit.

In FIG. 2A, a schematic representation is given of a SA alkylation unit as described in FIG. 1, which was revamped using the method according to the invention, wherein a second separator unit suitable for the separation of solids from liquids is provided. In FIG. 2A, part or all of the catalyst phase can be diverted from catalyst phase recycle conduit 145 by conduit 405 to centrifuge 410. In centrifuge 410, solids are removed from the IL catalyst phase under influence of the centrifugal forces, and are retrieved via conduit 415. The remaining IL catalyst phase exits centrifuge 410 via conduit 420, which is in fluid connection with catalyst phase recycle conduit 145.

Figure 2B:
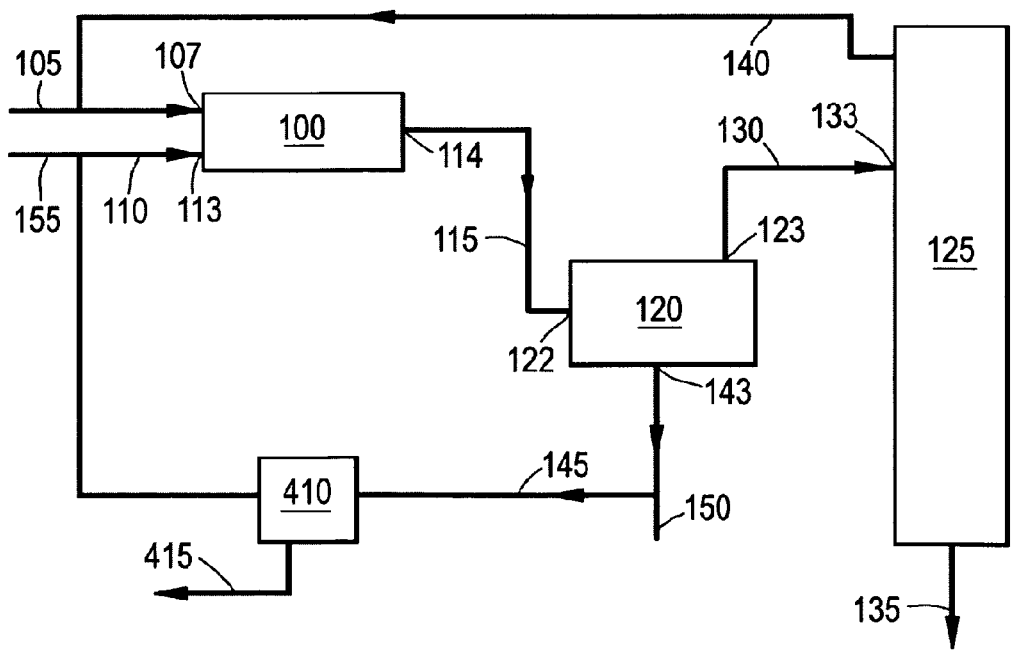
FIG. 2B illustrates a schematic representation of an SA alkylation unit.

In FIG. 2B, a schematic representation is given of a SA alkylation unit as described in FIG. 1, which was revamped using the method according to the invention comparable to that in FIG. 2A. However, in FIG. 2B, centrifuge 410 was incorporated directly in catalyst phase recycle conduit 145.

Where FIGS. 1 and 2 refer to a SA alkylation unit, it will be appreciated that the same drawings could be used to represent an HF alkylation unit.

EXAMPLES

The invention is illustrated by the following non-limiting examples.

Example 1

An alkylation process was performed in three separate runs to mimic regular solids removal. In between each run the acidic ionic liquid catalyst was separated from the hydrocarbon phase and treated by removing solids and adding hydrogen chloride gas. The treated acidic ionic liquid catalyst was subsequently used in the following run.

The catalyst used was an ionic liquid catalyst comprising a coordinate anion derived from aluminium(III) chloride and copper(I) chloride (ex China University of Petroleum Beijing).

At start-up, sufficient isobutane was provided to the test unit to allow for a molar ratio of isoparaffin to olefin in the reactor of above 95.

A hydrocarbon mixture of isobutane and butenes was provided together with the acidic ionic liquid catalyst to the alkylation reactor. The reactor had a volume of 0.4 liter.

The effluent of the alkylation reactor was separated in a settler and part of the hydrocarbon phase was sent to a fractionator, while the remainder of the hydrocarbon phase was recirculated to the reactor.

The alkylate was obtained from the bottom of the fractionator and tested to determine the motor RON and MON values.

An isobutane-comprising stream was recycled from the fractionator back to the hydrocarbon mixture.

The acidic ionic liquid catalyst phase obtained from the settler was recycled to the reactor. Periodically, i.e. between the runs, the acidic ionic liquid catalyst phase obtained from the settler was redirected to a disk centrifuge and centrifuged at 20000 rpm for 1 hour at a temperature of 50° C. The weight of solids produced was recorded. Following the solids removal, hydrogen chloride gas was added to the treated acidic ionic liquid catalyst at a pressure of approximately 5 bar at a temperature of 35° C., until no hydrogen chloride was consumed any more. The amount of hydrogen chloride consumed was recorded. The reaction condition and obtained results are listed in Table 1.

It will be clear that:

By providing means to recycle part of the hydrocarbon phase from the separator unit to the reaction recirculation a high isoparaffin to olefin molar ratio in the reactor is achieved. Recycling the isoparaffin from the fractionator alone cannot provide a high ratio of over 95.

By providing a second separator unit suitable for the removal of solids from the ionic liquid catalyst, approximately 1.5 kg of solids could be removed from the process. In case no solids removal would have taken place the 1.5 kg of solids would have accumulated in the reactor. By removing the solids, solids content is significantly reduced and the alkylate quality remains high.

By providing a means for acid injection into the catalyst recycle, the ionic liquid catalyst was intermittently rejuvenated, by reacting with hydrogen chloride. As a result catalyst activity and the alkylate quality remains high.

The observed differences in the obtained alkylate properties are caused by the differences in the alkylation temperature and isoparaffin to olefin ratio.

TABLE 1

| Run | | 1 | 2 | 3 |
|---|---|---|---|---|
| Reaction temperature, | ° C. | 35.7 | 41.0 | 35.9 |
| isobutane/butene ratio in feed* | mol/mol | 5.3 | 11.3 | 11.6 |
| Ionic liquid/hydrocarbon ratio | vol/vol | 1.08 | 1.06 | 1.06 |
| Feed flow rate, | kg/h | 1.5 | 1.9 | 1.9 |
| Runtime, | h | 67 | 52 | 53 |
| Fresh C4 feed, | kg | 101.8 | 99.5 | 101.6 |
| Fresh feed composition | mol % | | | |
| propane | | 0.1 | 0.1 | 0.1 |
| isobutane | | 56.7 | 50.6 | 52.1 |
| n-butane | | 8.7 | 10.9 | 9.0 |
| 1-butene | | 1.6 | 2.2 | 1.6 |
| 2-butene (trans) | | 20.8 | 22.0 | 23.4 |
| 2-butene (cis) | | 8.9 | 10.5 | 10.0 |
| i-butene | | 3.0 | 3.2 | 3.2 |
| Alkylate, | kg | 73.3 | 81.6 | 90.4 |
| Engine tested RON | | — | 90.5 | 94.0 | 95.0 |
| Engine tested MON | | — | 90.2 | 91.8 | 92.7 |
| Total solids** | g | 729.3 | 435 | 376 |
| Hydrogen chloride consumption | g | 143 | 95 | 104 |

*isobutane/butene ratio, i.e. the isobutane/butene ratio in the mixture of fresh feed and the isobutane recycled from the fractionator
**total weight of the solids slurry Solids Analysis The solids removed from the acidic ionic liquid catalyst phase were analysed. The size distribution was determined using a laser particle size analyser.

The results are shown in Table 2.

TABLE 2

| Run | | 1 | 2 | 3 |
|---|---|---|---|---|
| Percentage of particles having a diameter below 5 μ | % | 99 | 99 | 99 |
| Percentage of particles having a diameter below 3 μ | % | 80 | 81 | 80 |

What is claimed is:

1. A method for revamping an HF or sulphuric acid alkylation unit to an ionic liquid alkylation unit, wherein the HF or sulphuric acid alkylation unit comprises a reactor unit for contacting catalyst and hydrocarbon reactants;

a separator unit for separating a reactor effluent into a catalyst phase and an alkylate-comprising hydrocarbon phase; and a fractionator unit for fractionating the alkylate-comprising hydrocarbon phase into at least one stream comprising alkylate;

which method includes the steps of:
- replacing the HF liquid catalyst or sulphuric acid liquid catalyst in said HF or sulphuric acid alkylation units with an ionic liquid catalyst;
- providing a second separator unit suitable for the separation of solids from liquids downstream of the reactor unit; and
- separating and removing solids from at least part of the ionic liquid catalyst-comprising reactor effluent in said second separator unit to reduce the solids content in at least part of the reactor effluent.

2. A method according to claim 1, wherein catalyst phase recycle means are provided to recycle at least part of the catalyst phase from the catalyst phase outlet of the separator unit to the reactor unit and wherein the second separator is integrated in the catalyst recycle means.

3. A method according to claim 2, wherein the second separator unit is a filtration, precipitation and/or centrifugation unit.

4. A method according to claim 3, wherein the second separator comprises an outlet for a solids-comprising stream and means are provided to further treat a solids-comprising stream.

5. A method according to claim 1, wherein solids are separated and removed from the catalyst phase in said second separator to the extent that the reactor unit comprise at the most 5 wt % solids, based on the total weight of the ionic liquid catalyst in the reactor unit.

6. A method according to claim 1, wherein catalyst phase recycle means are provided to recycle at least part of the ionic liquid catalyst phase to the reactor unit, and the solids are removed from the ionic liquid catalyst phase prior to reintroducing the catalyst phase to the reactor unit.

7. A method according to claim 4, wherein the solids-comprising stream from the second separator is extracted with a solvent to recover residual ionic liquid.

8. A method according to claim 5, wherein solids are separated and removed from the catalyst phase in said second separator to the extent that the reactor unit comprise at the most from 0.1 to 2 wt % solids, based on the total weight of the ionic liquid catalyst in the reactor unit.

9. A method according to claim 5, wherein the solids have an average particle size of from 0.1 to 10 μm.

* * * * *